United States Patent [19]

Kistner et al.

[11] Patent Number: 6,142,974
[45] Date of Patent: Nov. 7, 2000

[54] PORTABLE I.V. FLUID WARMING SYSTEM

[75] Inventors: Thomas L. Kistner; Robert W. Storey, both of Richardson; Daniel T. Kistner, Van, all of Tex.

[73] Assignee: Estill Medical Technologies, Incorporated, Dallas, Tex.

[21] Appl. No.: 09/156,324

[22] Filed: Sep. 18, 1998

[51] Int. Cl.$^7$ .................................. A61F 7/12; F24H 1/10
[52] U.S. Cl. ........................... 604/113; 604/114; 392/479
[58] Field of Search .................................. 604/113, 114; 392/470, 472, 480, 485, 489, 490, 479; 219/528

[56] References Cited

U.S. PATENT DOCUMENTS

| | | | |
|---|---|---|---|
| 3,370,153 | 2/1968 | Du Fresne et al. | 219/302 |
| 3,443,060 | 5/1969 | Smith | 219/302 |
| 3,551,641 | 12/1970 | Truhan | 219/303 |
| 4,314,143 | 2/1982 | Bilstad et al. | 219/497 |
| 4,532,414 | 7/1985 | Shah et al. | 219/308 |
| 5,254,094 | 10/1993 | Starkey et al. | 604/113 |
| 5,381,510 | 1/1995 | Ford et al. | 392/470 |
| 5,875,282 | 2/1999 | Jordan et al. | 392/470 |

FOREIGN PATENT DOCUMENTS

| | | | |
|---|---|---|---|
| 8704887 | 8/1987 | WIPO | 219/302 |

*Primary Examiner*—Ronald Stright
*Assistant Examiner*—Michael J. Hayes
*Attorney, Agent, or Firm*—Jones, Day, Reavis & Pogue

[57] ABSTRACT

A portable intravenous fluid warming system wherein the temperature monitoring and control is accomplished utilizing four monolithic IC thermosensors. The sensors operate in a serial multi-stage fashion with the first sensor functioning so as to provide a ramp or build up to the next stage thus smoothly and gently increasing the temperature of the fluid and reducing the dynamic range required for the final heater stage, thus ensuring a more accurate and consistent output temperature. Power FET's provide heater drive current from an unregulated DC input source. The sensor is coupled to a microprocessor that is factory preprogrammed with predetermined set points. The microprocessor will continuously determine the temperature so as to allow determination of when the desired temperature is reached and will adjust power to the FET as necessary to hold the temperature at the correct point without exceeding the temperature. Interfacing is provided to an optional external digital readout unit for monitoring. The addition of an in-line thermocircuit breaker will provide an independent over-temperature shutdown failsafe.

23 Claims, 5 Drawing Sheets

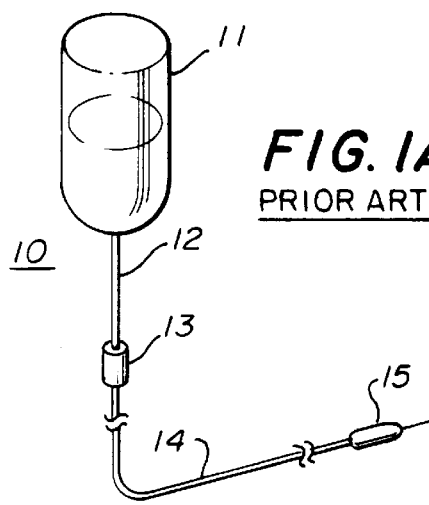
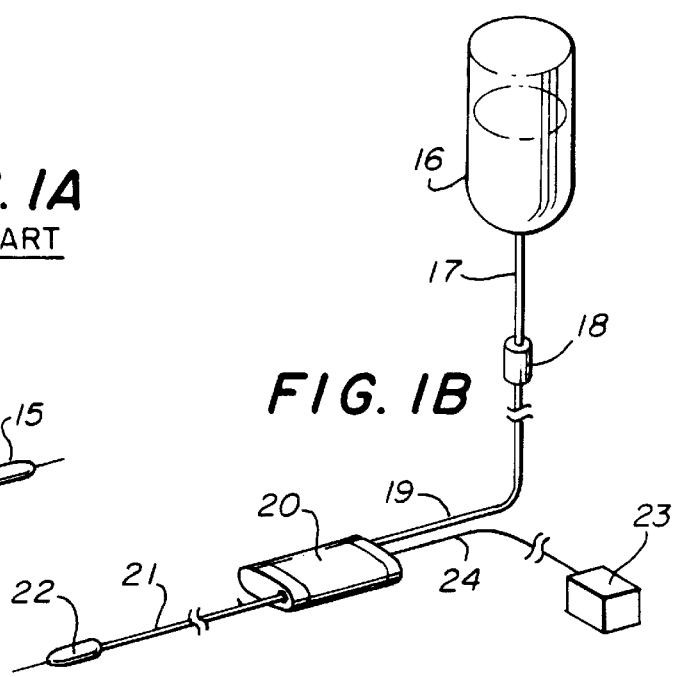
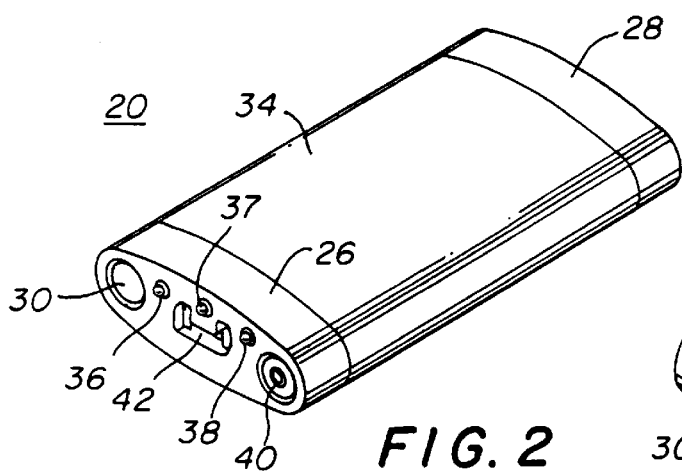
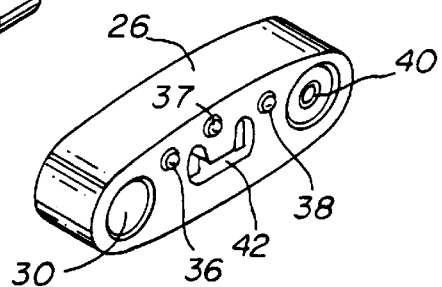
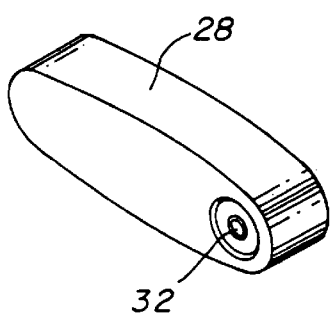
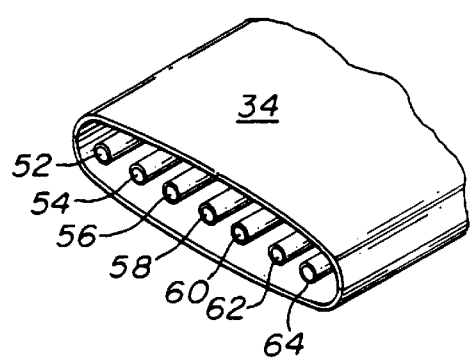

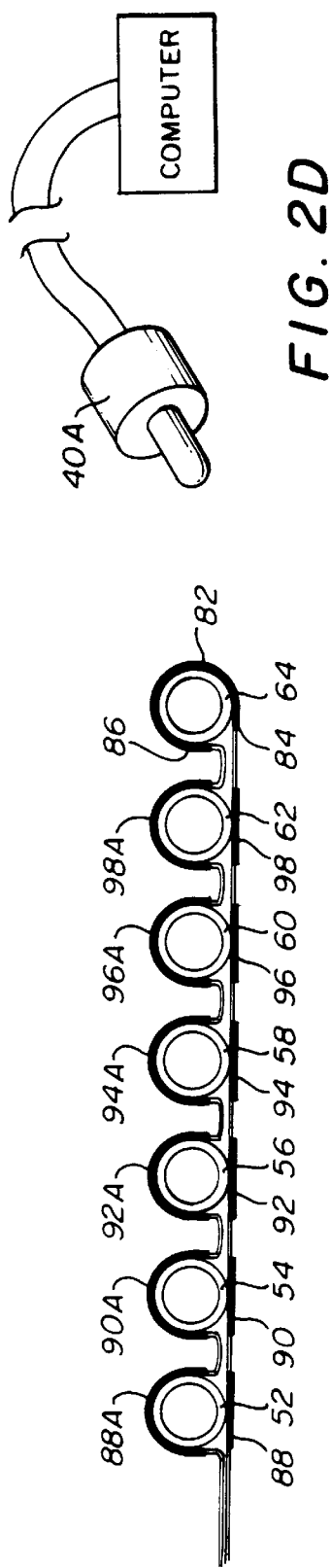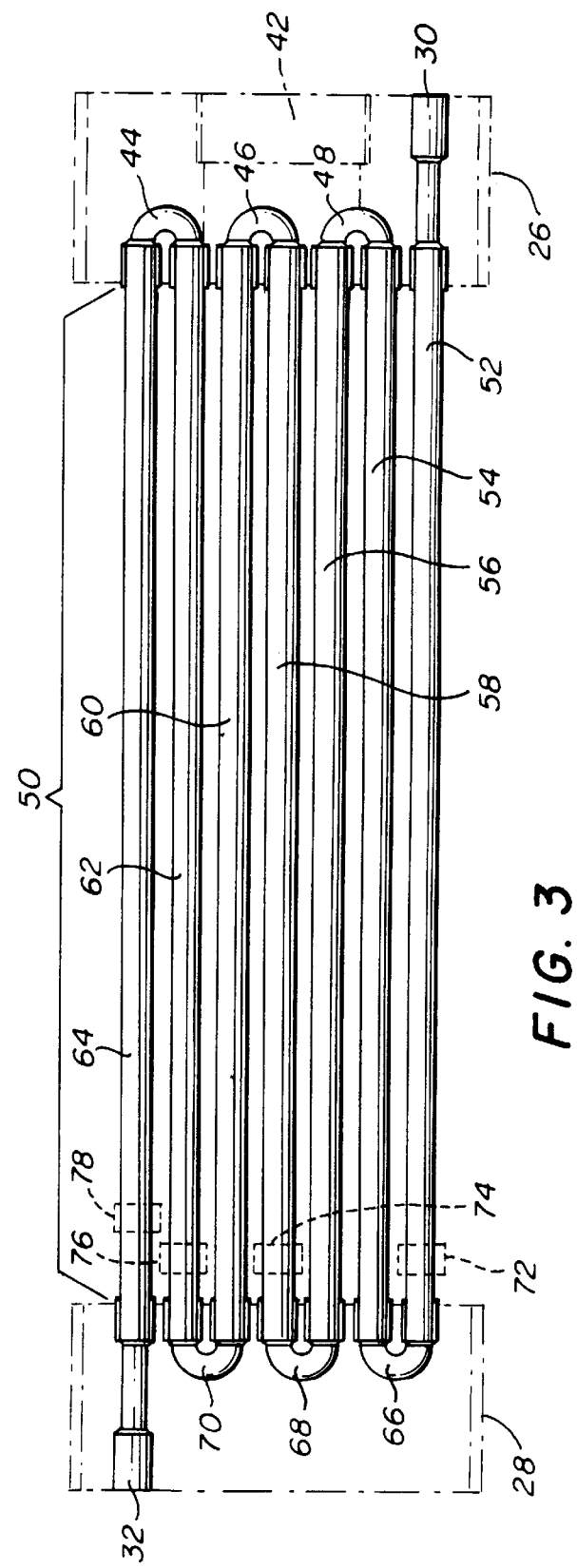

PORTABLE I.V. FLUID WARMING SYSTEM

BACKGROUND OF THE INVENTION

1. Field of the Invention

The present invention generally relates to an apparatus to warm fluids meant to be infused into the body, including blood products, to a desired temperature, approximately the normal body temperature. This apparatus is small, portable, and disposable and is easily used by the care giver without special training.

2. Description of Related Art Including Information Disclosed Under 37 CFR 1.97 and 1.98

Fluid introduced intravenously should be warmed to a temperature approximating normal body temperature to prevent the lowering of core body temperature. Intravenous fluids are normally stored at ambient temperature with some products stored at refrigerated temperatures. Normal core body temperature is 98.6° F. (37° C.), ambient temperature is 75° F. (23.9° C.) and refrigerated temperatures are from 32° F. to 40° F. (0° C. to 4.4° C.). In emergency situations, such intravenous fluids may necessarily be introduced at refrigerated temperatures directly into the body through intravenous (I.V.) tubes. Introduction of such liquids at these refrigerated temperatures, however, presents a substantial risk for injurious chill hypothermia and/or shock to the body.

A variety of devices have been developed to address the issue of the warming of intravenous fluids. Current systems are generally of two types. Bulk warmers require a sufficient period of time to warm the product to a desired temperature and will only warm up a set number of fluid units at a time. Moreover, in order for the bulk warmer to be constantly ready for emergency use, it must be maintained at a proper and set temperature. This requires a system which is bulky, heavy, and/or fixed. Prewarming and holding such fluids, as set forth above, is not practical for certain blood products and pharmaceuticals that are degraded if held at an elevated temperature.

Moreover, the bulk warmers allow the fluid to cool in the line set as it is administered. A bulk warmer system also experiences drawbacks associated with emergency use since it requires prior anticipation of the need for warmed fluid units as well as the number of fluid units which will ultimately be needed. Furthermore, and assuming the aforereferenced conditions are met, fluid units that are warmed and ready for use must move through several feet of tubing in addition to the drip chamber thereby offering substantial time and opportunity for such liquids to cool before entering the body.

The second type are in-line fluid warmers. Previous in-line fluid warmers somewhat address the disadvantages described above except that such in-line systems attempt to warm the fluid in the existing plastic line, which is an inefficient means of heat transfer. Moreover, in-line warming systems are generally limited in volume, e.g., 30–40 millimeters per minute, and require a 120-volt AC power source. Additionally, the accuracy of such a system is only plus or minus 5 degrees. They are also bulky and require significant time to set up.

One such system is known as the Animec Infusion Warmer. It is electrically powered and is a dry warmer that supplies external heat to plastic tubes by an aluminum heating plate. Temperature sensors contact the tubing and regulate the temperature. The plastic tube to be heated can be placed in an S-shaped channel in the heating plate in the warmer. Different size tubes can be used. This unit has several disadvantages. First, the length of tubing being heated is comparatively short. Second, the tubing is contacted by the aluminum plate over only a portion of its surface area. Third, total heating of the heating plate is based only on the output temperature of the fluid. Fourth, different models must be used for different sized tubing. Fifth, it is not portable but requires a 110-volt AC power source. Sixth, it is possible that excessive warming of the fluid can occur. Seventh, it is not a disposable warming unit.

SUMMARY OF THE INVENTION

The present invention addresses the above and other disadvantages of prior art systems for warming intravenous fluids.

The preferred embodiment of the invention comprises a tube network containing parallel straight sections in the same plane, wrapped in a flexible material which supports resistance heater elements. The inlet cap or manifold contains the power supply connector, data input/output jacks, fluid inlet connectors, and LED's for power and temperature indicators. These various connectors are connected to corresponding components on a flexible printed circuit card and the components mounted thereon. The outlet cap or manifold holds the fluid outlet connector and forms a watertight seal with the main body of straight parallel tubes. The fluid line connectors are standard size to fit standard I.V. line connections. The power source is a portable batter, vehicle/aircraft power supply, or standard 120 AC power. The power source will connect into a jack on the inlet end cap or manifold as shown, or any other convenient location in the housing.

In the preferred embodiment, the heating elements are divided into four groups that are connected in electrical parallel. However, more groups or even fewer groups could be used if desired. Each of the groups has a plurality of heating elements connected in electrical series with each heating element being in direct heat transfer relationship with a corresponding one of the appropriate tubing sections.

A first temperature sensor senses the temperature on the first tube after incoming I.V. fluid enters on the entrance side. Additional temperature sensors monitor the temperature in each heating group and a final sensor monitors the temperature as the fluid leaves the last tube. Each sensor is operatively coupled to a central microprocessor which, in turn, adjusts the power to the heating elements in each heating zone to maintain a constant output temperature.

Appropriate light-emitting diodes indicate when the power is ON and when the power is connected to the various groups of heating elements.

Thus, the present invention presents a number of advantages over the prior art. One such advantage is the ability to quickly warm an unlimited amount of fluid within a specific temperature range.

Another advantage presented by the invention is the reduction in heat loss after the fluid is warmed by heating the fluid close to the point of entry into the patient's body.

Still another advantage of the present invention is ready adaptation and application to conventional I.V. line-set assemblies. In such a fashion, economy of energy is observed while assembly and interconnection may be accomplished in a short amount of time.

Also, another advantage of the present invention lies in its low cost construction thereby enabling a disposable use. In such a fashion, a sterile environment is ensured for each use.

Yet another advantage is the adaptability of the present invention to emergency field conditions without loss of time in treatment or in transport.

A further advantage of the invention is that the entire unit is in one piece, without a separate, reusable, control unit.

Still other advantages of the present invention will become obvious after review of the detailed description of the drawings.

Thus, the invention relates to a portable intravenous fluid warming system comprising a housing having an I.V. fluid input port and an I.V. fluid output port, a plurality of interconnected stainless steel tube sections in the housing carrying the I.V. fluid to be warmed from the fluid input port to the fluid output port, each one of the tube sections having an outer periphery, groups of the tube sections being coupled to the input port in the housing for receiving I.V. fluid to be warmed, at least a first group of said multiple groups of tube sections forming a group of staged heating sections, a final tube section being coupled to the output port in the housing for dispensing the warmed I.V. fluid and forming a final heating stage, and a like number of flexible heating elements as the plurality of tube sections for heating the I.V. fluid therein, each one of the flexible heating elements being wrapped around, in contact with, and surrounding at least the majority of the peripheral surface of a corresponding tube section.

BRIEF DESCRIPTION OF THE DRAWINGS

These and other features of the present invention will be more fully disclosed when taken in conjunction with the following Detailed Description of the Preferred Embodiment(s) in which like numerals represent like elements and in which:

FIG. 1A illustrates the elements of a conventional I.V. system;

FIG. 1B illustrates the various elements of one preferred embodiment of the present invention;

FIG. 2 is a perspective view of one embodiment of the portable, disposable fluid warming unit incorporating the teachings of the present invention;

FIGS. 2A and 2B are perspective views of the fluid inlet end cap and fluid outlet cap respectively of the embodiment of FIG. 2;

FIG. 2C is a perspective view of the central body portion of the embodiment of FIG. 2;

FIG. 2D illustrates a computer with a connector suitable for connecting to the embodiment of FIG. 2;

FIG. 3 is a top schematic view of the embodiment of FIGS. 2, 2A, 2B, and 2C showing a phantom view of the outside casing of the fluid inlet and outlet manifolds and without the central body casing thereby revealing the tubing section;

FIG. 4 illustrates a cross-sectional view of the tubes and the method of wrapping heating elements to make the heat exchanger of the warming blanket of the embodiment of FIG. 2;

DETAILED DESCRIPTION OF THE PREFERRED EMBODIMENT(S)

Figure 5:
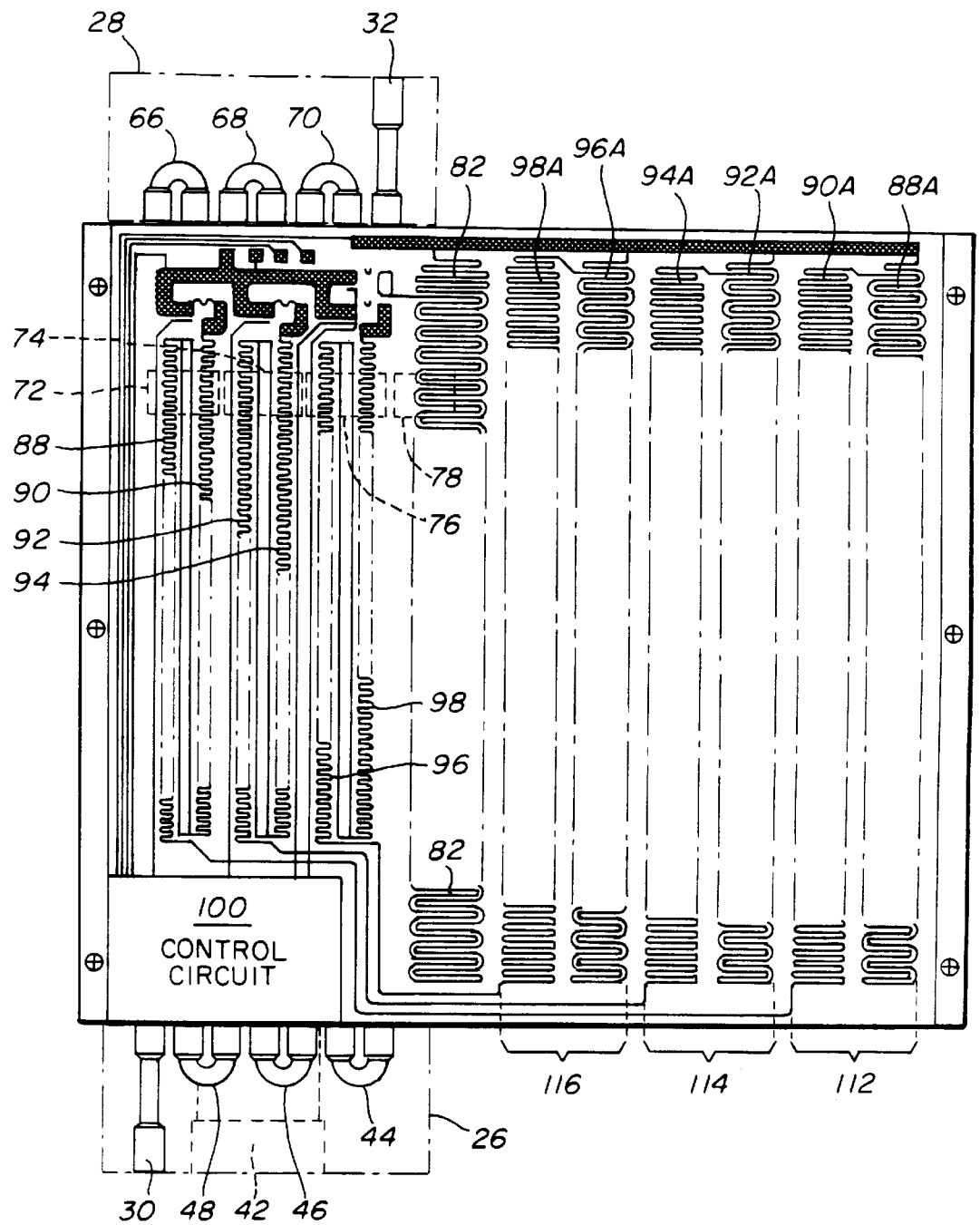
FIG. 5 is an unfolded layout of the electrical heating elements of the warming blanket or printed circuit used in the embodiment of FIG. 2.

An illustration of a conventional intravenous setup 10 may be seen by reference to FIG. 1A. As illustrated in FIG. 1A, an intravenous solution, e.g., a saline solution, is contained in a bag or bottle 11 which is normally suspended above the patient. Fluid from the bag 11 passes by gravity or positive pressure through a conduit or tube 12 into a drip chamber 13 whereupon the flow rate is monitored. Fluid passes from drip chamber 13 through a second conduit 14 that is coupled to a catheter 15 to be inserted into selected blood vessels of the body.

The aforedescribed intravenous system has been used as a standard method of administering intravenous fluids and blood and blood products. These products are administered at the temperature at which they are stored (ambient temperature or from refrigerant storage). In some cases, they are prewarmed and then administered allowing them to again cool toward ambient temperature while being administered.

Other intravenous fluids, such as blood products, must be maintained at a refrigerated temperature of 40° F. (5° C.) or less immediately prior to being administered to the patient. Moreover, the flow rate at which such products must be introduced to the body forecloses their use unless or until warmed near body temperature.

The present invention is intended to overcome these disadvantage and is designed to be operated by field emergency medical technicians (paramedics) trained in administering I.V. fluids under adverse conditions. The normal patients are the victims of trauma or serious acute illness with a substantial potential of progressing into hypothermia and shock. Fluids may be administered under adverse conditions such as to individuals trapped in vehicles or collapsed buildings as well as in other cluttered and chaotic field conditions. These settings dictate small, easily handled mechanisms that do not add to the confusion and difficulty of the situation.

Since most trauma and acute illnesses happen in environments of considerably less than body temperature, virtually all patients requiring I.V. solution will have the potential of entering shock while being handled in emergency channels. Control of I.V. fluid temperatures would be appropriate. Certainly, all patients requiring the addition of a significant volume of fluid should receive fluids at body temperature. Such a system must warm I.V. fluids to a range of 98.6° to 104° F. (37° to 40° C.) and must infuse the fluid into a patient at the rate of up to 200 ml per minute. There must be no danger of malfunction causing overheating of the fluid being infused. The equipment involved must be lightweight and easy to handle (idiot proof) in confmed areas in all weather and environmental conditions. The system must be sterile and any parts coming in contact with a patient must be disposable. The system must be compatible with existing I.V. fluid systems and must be capable of being made ready within one minute with only a minimum of additional steps being required over the standard system. The system must be usable as close as possible to the patient when starting I.V. solution to prevent re-cooling of the I.V. fluid. The operating time before a change in the power source is required to be a minimum of 30 minutes under normal expected uses. Further, the warming system must be independent of the I.V. solution bag temperature.

The I.V. fluid warming system of the present invention provides an outlet temperature in the range of 98.6° F. (37° C.) to 104° F. (40° C.). The maximum temperature is approximately 105° F. (40.6° C.). A shutdown occurs at any desired preset temperature, such as 105° F. (40° C.). The unit will handle a flow rate up to 200 ml per minute from 70° F. (21° C.) to 98.6° F. (37° C.) or at smaller flow rates at lower temperatures. The unit can be used in all weather and is a disposable unit. It is compatible with existing I.V. fluid systems and takes approximately 30 seconds to set up. Power can be supplied either from a 12-volt battery, a 12-volt DC adapter or an AC adapter. An optional external digital readout may be provided with an external monitor attached to a data connector jack.

The data connector may also be used to connect a temperature adjustment device for use by appropriate medical personnel when needed. The connector may also be used to connect to a computer to monitor details of temperature and power in each of the stages of the heater with the data transferred to a computer program such as the well-known EXCEL program.

Thus, as can be seen in FIG. 1B, a preferred embodiment of the present invention as it may be incorporated into the aforedescribed conventional intravenous system in order to warm the solution prior to administration to the patient is shown. Fluid from an I.V. bag or bottle 16 passes through a conduit 17 to a drip chamber 18 as described above in conjunction with a conventional intravenous system illustrated in FIG. 1A. Fluid then passes through a second conduit 19 into the system 20 of the present invention which comprises a fluid warming element. The warmed fluid then passes through a third conduit 21 that is coupled at its terminal end to a catheter 22 to be inserted into the body. A power supply 23 provides power through a conductor 24 to the unit 20. Alternatively, the unit 20 may be connected to a converter connected to standard AC power or to a vehicle power source directly or through a portable battery.

It will be understood from the system in FIG. 1B that the warmer 20 may be provided very close to, or even placed on, the body of the patient. Thus, the tube 21 is short and allows for little heat loss prior to the fluid entering the patient's body.

FIG. 2 is a diagrammatic representation of the warming unit 20. It has plastic end caps or manifolds 26 and 28, shown in detail in FIG. 2A and FIG. 2B, that pass the incoming fluid through a port 30 in end piece 26 back and forth through warming tube sections as shown in FIG. 2C and then to an outlet port 32 in end piece 28 as shown in FIG. 2B. The end caps or manifolds 26 and 28 have their connections to the I.V. lines recessed for protection. The central body portion 34 as shown in FIG. 2C includes the tube sections which, when combined with the manifolds 26 and 28, form a continuous channel from the entrance 30 to the exit 32. As will be shown and discussed in detail hereafter, the tubes are wrapped by a special warming blanket or flexible printed circuit containing the heating elements that can be wrapped or formed around the tubes.

The entire unit is encased in a protective covering such as a plastic extrusion such as is illustrated in FIGS. 2A, 2B, and 2C. Light-emitting diodes 36, 37, and 38 indicate selected operating functions of the device. According to one embodiment, LED 36 may indicate power being supplied to the various stages and LED 38 may indicate the status of the power source such that the light intensity of the diode decreases as the input power voltage decreases. There is also an input power jack 42 and a data port connection 40. It will also be appreciated that the warmer of the present invention could be used for continuous arteriovenous blood warming. For those warmers identified for such use, heparin may be used to coat those portions of the device which will contact the blood to prevent the possibility of blood clotting.

FIG. 3 illustrates in a schematic way the individual tube sections coupled to the end portions in a circuitous and serpentine fashion. Thus, it can be seen that end portions 26 and 28 have input and output ports 30 and 32, respectively. Further end cap 26 includes arcuate tube portions 44, 46, and 48 which may be a bent continuous tube or could function as a manifold at the inlet end of the plurality of straight parallel tubes indicated generally at 50 in FIG. 3, and shown separately in FIG. 2C as tubes 52, 54, 56, 58, 60, 62, and 64. Similarly, end cap 28 also includes arcuate tube portions 66, 68, and 70 which may be a bent continuous tube or could function as a manifold at the outlet end of the plurality of straight parallel tubes 50. Thus, the fluid flow path from the input port 30 to the output port 32 is a circuitous serpentine path through parallel spaced tube sections 50 in a horizontal plane. Circuit element 72, as shown diagrammatically by a box 72 in phantom lines in FIG. 3, represents temperature sensor 72 shown in FIGS. 5, 6, or 7 for the incoming fluid heating stage and element. Sensors for the intermediate heating stages are represented by boxes 74 and 76 shown in phantom lines in FIG. 3 and sense temperatures in those stages. Box 78, shown in phantom lines, represents the sensor for the outgoing or final fluid heating stage. The temperature sensors are shown here merely to indicate their relative placement in the housing. They would all be physically placed in the housing at a location most convenient for the connections. While seven tube sections are shown in FIGS. 2 and 3, it will be understood that more or less tube sections may be used as desired for a particular warming device.

Figure 6:
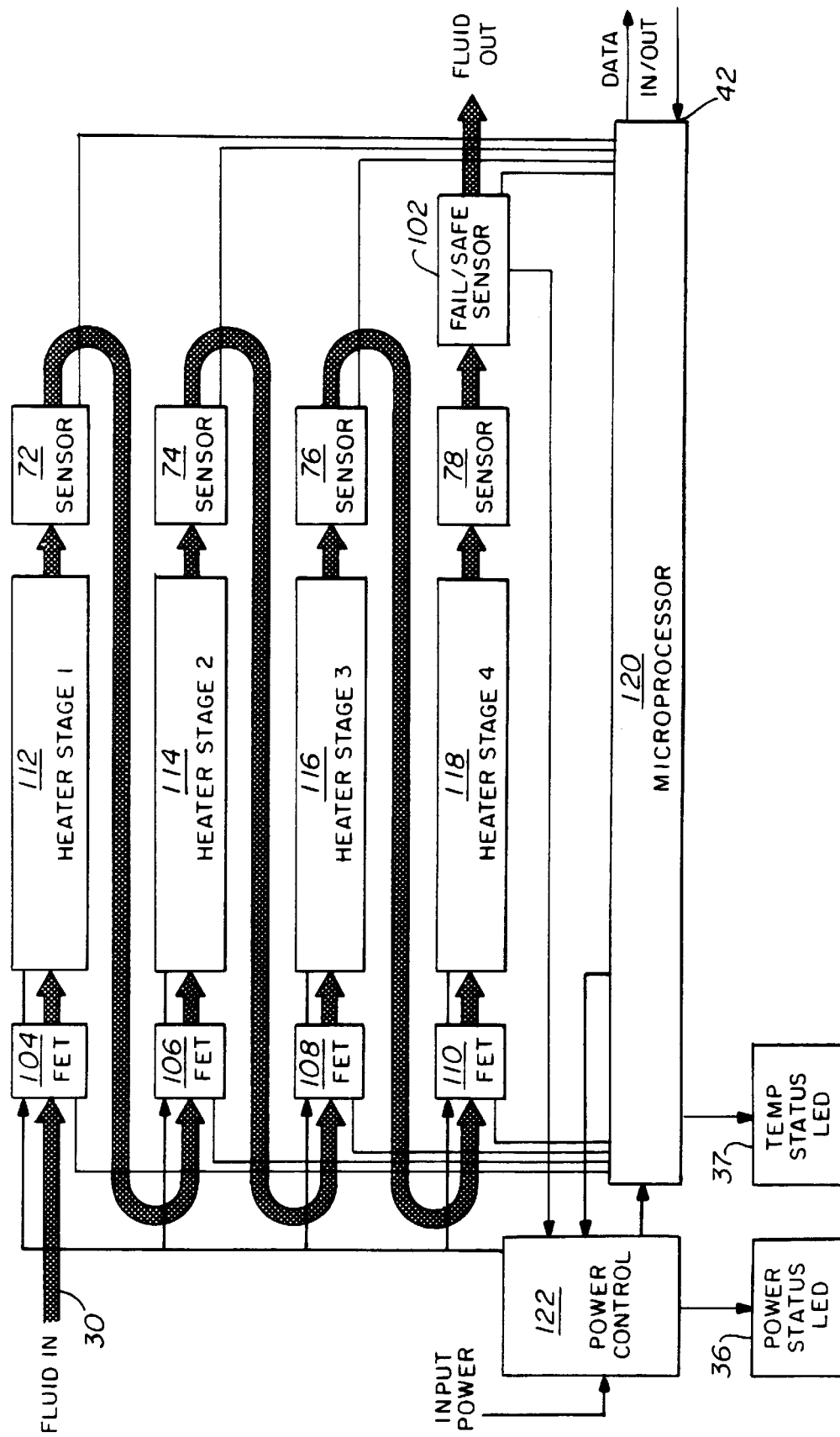
FIG. 6 is a diagrammatic representation of various electronic components along with the warming blanket or printed circuit with the flexible heating elements thereon in relation to the tube sections that are to be heated.
Figure 7:
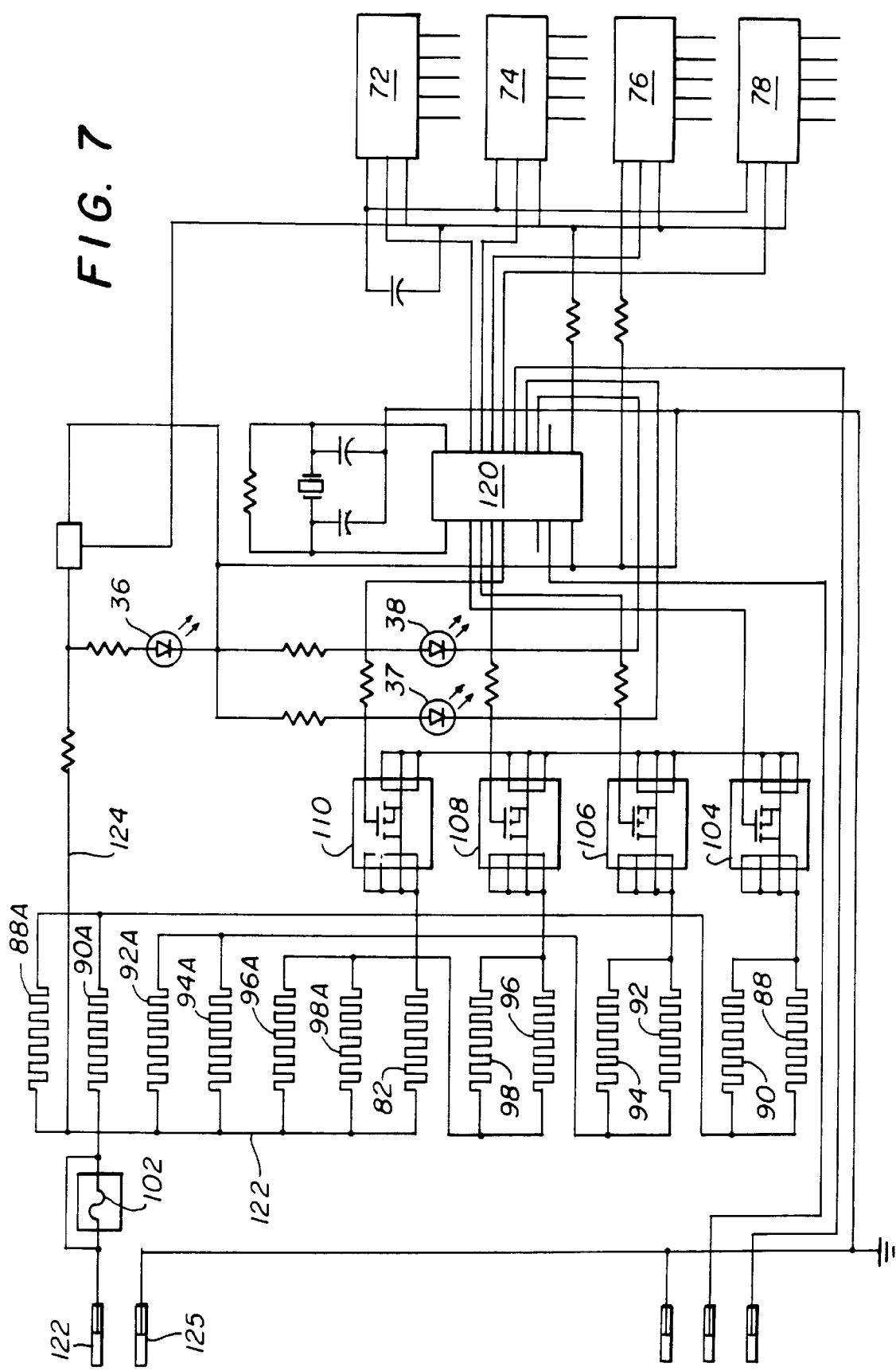
FIG. 7 is a wiring diagram of the electrical circuit of the present invention.

FIG. 2A is a view of the inlet end cap or manifold 26 with the power connector 42, incoming fluid line 30, data connection port 40, power LED 36, and LED 37 which indicates which heating elements are functioning, and LED 38 which will indicate fluid temperature status by varying its flashing rate depending upon the temperature. According to one embodiment these elements are molded into the end cap or manifold 26 by injection molding. The electrical connections extend through the end cap so they can be surface mounted to their proper connections on the warming blanket or printed circuit card or other components as shown in the views of FIGS. 6 and 7.

FIG. 2B is a perspective view of the outlet end cap or manifold 28 for receiving the outgoing fluid line 32.

FIG. 2C is the central or main body portion 34 showing the tubes 52, 54, 56, 58, 60, 62, and 64. The heating blanket is not shown. The two end caps or manifolds shown in FIGS. 2A and 2B will form a seal between the caps or manifolds and the main body portion shown in FIG. 2C.

FIG. 2D shows a connector 40A for connecting a monitoring and/or control device 43, such as a computer, a recorder or the like to the fluid warmer 20 of this invention through connector port 40.

FIG. 4 is a diagrammatic representation of a cross-sectional view of the warming unit at a point where the tubes are covered by the warming blanket or heating elements (printed circuit card). Each of the tube sections 52, 54, 56, 58, 60, 62, and 64 is shown. Note that under the bottom of each of the tubes, except for the last tube 64, is a corresponding heating element 88, 90, 92, 94, 96, and 98, respectively, and further illustrated in FIG. 5. With respect to the edge or last tube 64, the flexible heating element 82 begins under the tube 64 at 84 and extends around the remaining peripheral surface of tube section 64 as shown at 86 and is in heat transfer relationship therewith. The remainder of the printed circuit has heating elements 88A, 90A, 92A, 94A, 96A, and 98A that wrap around and surround the remainder of the peripheral surface of the corresponding six remaining tube sections. Also inside the central body portion 34 shown in FIG. 2C are the electronic circuits, shown collectively by reference number 100 in FIG. 5, electrically coupled to power jack 40. Thus, the printed circuit substrate or warming blanket is flexible, has the flexible heating elements thereon, and forms a special warming blanket that is molded around the tubes as shown with the heating elements formed on the substrate or warming blanket as will be shown more clearly in FIG. 5. The flexible substrate may be, for example only, Mylar or some other suitable flexible material. Although not shown, for some uses an additional insulating layer of material may be placed over the special warming blanket to hold the heat in the unit.

In one preferred embodiment, the tube sections 50, as shown in FIG. 3 are stainless steel tubes formed of a medical grade stainless steel, e.g., 316L or 304L grade. Other tubing material with high thermal conductivity and medical grade coating may also be used. Heating is accomplished with the resistive heaters 88A, 90A, 92A, 94A, 96A, and 98A, base heaters 88, 90, 92, 94, 96, and 98, and wrap-around portion 82 etched on the flexible circuit material such as Mylar in a well-known manner. The flexible material is formed around each tube as shown in FIG. 4. Independent heating element circuits, which form stages or zones, are formed as will be discussed hereafter with respect to FIG. 5 establishing the heating stages which provide a major portion of the heat, and a final heating stage formed with heating element 82 completes heating to the desired temperature. While four independent heating zones are described herein, it will be understood by one skilled in the art that more (or even fewer) than four heating zones may be formed if desired. A separate temperature-sensitive circuit breaker (102 in FIG. 7) provides input power to the power circuit for interrupting the circuit if the preset safety temperature is reached. Additionally, excessive current to the main power circuit causes failure of the circuit thereby preventing overheating of the system.

Thus, FIG. 5 is a diagrammatic representation of the warming unit with the warming blanket or flexible printed circuit substrate being shown in its unfolded condition with the heating elements thereon and shown in relation to the tube sections that carry the intravenous fluid. The end portions 26 and 28 are shown with the tube sections 50 which include straight tube sections 52, 54, 56, 58, 60, 62, and 64 attached thereto so as to couple the fluid from input port 30 to output port 32. Tangent (as shown in FIG. 4) to each tube section, except the last tube 52, is a heating element 88, 90, 92, 94, 96, and 98. Under and continuing around each tube 52, 54, 56, 58, 60, and 62 are the heating elements 88A, 90A, 92A, 94A, 96A, and 98A, respectively, which include one-direction elements 90A, 94A, and 98A and bi-directional heating elements 88A, 92A, and 96A which double back on themselves and nest between the first line of bends. The last tube 64 is completely wrapped by one heating element 82 also doubles back on itself and is designed similar to heating elements 88A, 92A, and 96A.

In the preferred embodiment, heating elements 88A, 90A, 92A, 94A, 96A, and 98A are sufficiently wide so they can be wrapped around and substantially surround the peripheral surface of the remaining tubes such as shown in FIG. 4.

Four controlling FET's 104, 106, 108, and 110 are schematically shown in FIG. 7 coupled between the microprocessor chip 120 and the four stages of heating elements 112, 114, 116, and 118. They control the current by turning the power ON and OFF to the individual stages. Thus, the novel system of the present invention may be referred to as a "closed loop progressive integrated differential staged control system".

FIG. 7 is the schematic wiring diagram of the heating elements and the controllers shown in FIGS. 4, 5, and 6. Again, the circuit in FIG. 7 is shown as an example only and may include more or less than the four heating zones shown. As can be seen in FIG. 7, a power supply terminal 122 provides voltage through a circuit breaker 102 that will open at a predetermined temperature, or overcurrent, to prevent overheating of the intravenous fluid. The voltage is coupled on wire 122 to the various stages of heating elements in electrical parallel and is coupled as well to the thermosensors 72, 74, 76, and 78 by wire 124. Such thermosensors may be of the type sold by Dallas Semiconductor, Inc. under the designation DS1821. Control switches 104, 106, 108, and 110 (one each for each heating stage) are well known in the art and may be of the type known as IRF-7201 manufactured by International Rectifier, Inc. A battery or other power source is connected to the power jack and coupled between input terminal 122 and ground terminal 125 to provide the necessary power thereto.

In operation, when the unit 20 has the intravenous lines connected into and out of the unit and the fluid is flowing, LED 36 indicates the power is being received by the warmer unit. The intensity of LED 36 will also provide an indication of the battery or power supply status by decreasing in intensity as the voltage output drops. LED 37 indicates power is being sent to the heating elements through the four controllers or FET switches 104, 106, 108, and 110 which are being controlled by the microprocessor 120 based upon the temperatures received from the sensors. It indicates power is being supplied to the unit, and the tubes and the fluid are being heated. LED 37 may also be used to indicate the fluid temperature status by varying its flashing rate depending on the fluid temperature. Thus, for example only, by counting the number of flashes per minute, the temperature of the fluid in degrees Fahrenheit can be determined. LED 38 provides an indication that the fluid temperature is within an acceptable range. The temperature sensors 72, 74, 76, and 78 couple their outputs to microprocessor chip 120 that is programmed to determine the trend of temperature change and anticipate the amount of current necessary to maintain a preset temperature. At this point, the microprocessor 120, sensing low temperature intravenous fluid, turns ON FET switches 104, 106, 108, and 110 (one switch for each heating stage). Thus, the power is connected from the power source 122 through the circuit breaker 102 to the parallel heating stage's circuits. These elements can be seen in relation to the tube sections in FIG. 5. Thus, the input heater stage 112 is associated with the incoming fluid tube sections 52 and 54. The first intermediate heater stage 114 is associated with tube sections 56 and 58; the second intermediate heater stage 116 is associated with tubes 60 and 62, while the final heater stage 118 is associated with tube section 64. Again, tube sections may be added or subtracted as needed to meet specific requirements.

Incoming sensor 72 senses the preheated intravenous fluid at its location (shown at 72 in FIGS. 3 and 5) and, if the temperature is in a desired range (98.6° F. or 37° C. to 101.3° F. or 38.5° C.), a signal is generated that is sensed by microprocessor 120 that generates a signal that is coupled to switch 138 to open switch 104 and remove power to the input heater stage 112. In a like manner, if the intermediate thermostats 106 and 108, positioned as shown in FIG. 5 over the first intermediate heater stage 114 and the second intermediate stage 116 indicate that the temperature of the I.V. fluid is in the proper range, the appropriate switch 106 or 108 respectively disconnects the corresponding intermediate section. In a like manner, if thermostat 78 indicates the fluid leaving the warmer is in the proper temperature range, switch 110 opens and removes power from the final stage 118. When power is flowing to the heater elements, one of the LED's will be lit and will indicate the temperature status. When the battery power is at an acceptable level, another LED will be lit. If the temperature of the I.V. fluid exceeds a predetermined maximum temperature, fuse or circuit breaker 102 opens removing power to the unit. Likewise, for any heating stage which exceeds the temperature expected and the corresponding FET does not interrupt the current flow, breaker 102 will shut down the electrical circuit.

The presence of the microprocessor 120 allows the initial heating stage 112 and the two intermediate heating stages 114 and 116 to have dynamic set points which allow the most efficient energy use by providing a heating profile which follows a smooth ramp from the input temperature to the final stage. The fourth and final stage 118 will then have a fixed set point at the desired outlet temperature. The use of such dynamic set points provides for the possibility of a cooling capacity in the event the initial stage were to slightly overheat in the initial stage. The heating profile if graphed should form substantially a straight line from the incoming temperature to the preset outlet temperature. Consequently, the warmer of this invention will warm fluid to a preset temperature at any input/output rate (1 milliliter/minutes to 200 milliliters per minute) regardless of the incoming temperature or flow rate and maintain that temperature within ±2° F.

The condition of the four thermosensors, the power to the thermosensors, the ground connections, and the microprocessor 120 may be connected to data connector 42 that can be coupled to a remote analyzer or computer if desired. Consequently, the desired temperature for the output fluid may be adjusted by changing the settings in microprocessor 120. Typically, the data may be extracted from the microprocessor and displayed and/or recorded using clean text "ASCII" format. As an example, the temperature of each stage along with the percentage of available current for each stage along with the percentage of available current for each stage may be shown as it is measured. This may occur up to approximately 100 times per minute.

Thus, there has been disclosed a novel portable I.V. fluid warming system that is economical to construct, easy to operate, portable, disposable, and efficient in use.

The corresponding structures, materials, acts, and equivalents of all means or step plus function elements in the claims below are intended to include any structure, material, or act for performing the function in combination with other claimed elements as specifically claimed.

What is claimed is:

1. A portable intravenous fluid warming system comprising:
    a housing having an intravenous fluid input port and intravenous fluid output port;
    a plurality of groups of interconnected tube sections in said housing carrying said intravenous fluid to be warmed between said input port and said output port, each one of said tube sections having an outer periphery;
    a first group of said plurality of tube sections in said housing for receiving intravenous fluid to be warmed from said input port and forming a group of staged heating sections;
    a final section of tube in said housing for dispensing said warmed I.V. fluid to said output port and forming a final heating stage; and
    a like plurality of flexible heating elements as said plurality of tube sections for heating the intravenous fluid therein, each one of said flexible heating elements being wrapped around, in contact with, and surrounding at least the majority of the peripheral surface of a corresponding tube section.

2. The portable intravenous fluid warming system of claim 1 further comprising:
    first and second end portions on said housing having conduits therein for interconnecting said plurality of tube sections in a parallel, spaced, serpentine fashion in a horizontal plane from said input port to said output port, said tube sections having a top and a bottom.

3. The portable intravenous fluid warming system of claim 2 further comprising:
    a flexible printed circuit substrate having said flexible heating elements thereon;
    said flexible printed circuit substrate having sufficient length to enable a first portion of the substrate to be placed under each of said tube sections and a second portion to be folded over the top of each of said tube sections;
    a first plurality of heating elements on said first portion of said substrate for engaging a portion of the peripheral surface on the bottom of each tube section in heat transfer relationship except the input port tube section;
    a second plurality of heating elements on said second portion of said substrate, one of said second plurality of heating elements substantially encircling the input port tube section; and
    each of the remaining ones of said second plurality of heating elements being wrapped around and surrounding the remaining peripheral surface of a corresponding one of the remaining tube sections.

4. The portable intravenous fluid warming system of claim 3 further including:
    a power supply having a voltage and a ground potential;
    said first and second plurality of heating elements being coupled to said power supply in parallel;
    a first thermosensor for continually sensing the temperature of the intravenous fluid warmed by said first plurality of heating elements and generating an output signal representing the sensed temperature;
    a first switch coupled between said first plurality of heating elements and said power supply and coupled to said first thermosensor for disconnecting said first plurality of heating elements from said power supply to stop said heating when said predetermined temperature value is exceeded;
    a second thermosensor for continually sensing the temperature of the intravenous fluid warmed by said second plurality of heating elements and generating an output signal when the sensed temperature exceeds a preset value; and
    a second switch coupled between said second plurality of heating elements and said power supply and coupled to said second thermosensor for disconnecting said second plurality of heating elements from said power supply to stop said heating when said predetermined temperature value is exceeded.

5. The portable intravenous fluid warming system of claim 4 further including:
    a first LED for coupling to said power supply voltage to indicate when said power supply voltage is coupled to said heating elements; and a second LED coupled to said heating elements to provide an indication when said heating elements are heating.

6. The portable intravenous fluid warming system of claim 5 wherein said second LED further indicates the fluid temperature status by varying its flashing rate depending upon the fluid temperature.

7. The portable intravenous fluid warming system of claim 4 further comprising an external electrical connection panel on said housing for providing test connections to said sensors and said switches.

8. The portable intravenous fluid warming system of claim 4 wherein said tube sections are formed of stainless steel.

9. The portable intravenous fluid warming system of claim 1 further including:

a power supply having a voltage and a ground potential;

a switch coupled between said heating elements and said power supply for selectively coupling a voltage to said heating elements;

a heat sensor for sensing the temperature of said warmed intravenous fluid and continuously generating an output signal; and a microprocessor receiving said output signals to determine the trend of temperature change and controlling said switch to provide the amount of current necessary to maintain a predetermined temperature.

10. The portable intravenous fluid warming system of claim 4 wherein the heat sensor is placed in contact with the tube section connected to the output port to sense the output temperature of the intravenous fluid.

11. The portable intravenous fluid warming system of claim 9 further including a power interruption device coupled to said heating elements for disconnecting said heating elements from said power supply voltage if a predetermined excessive current flows through said heating elements.

12. The portable intravenous fluid warming system of claim 11 wherein said power interrupter device further disconnects said system from said power supply in the event said switch coupled between said heating element and said power supply fails to disconnect power upon command from said microprocessor.

13. The portable intravenous fluid warming system of claim 9 further comprising:

a flexible printed circuit substrate having said flexible heating elements thereon and said flexible heating elements comprising two groups of heating stages;

one of said two groups comprising at least two heating stages and cooperating with said microprocessor to provide a selected heating profile to said fluid ramping from the inlet temperature of the incoming fluid to a selected upper temperature; and the other said two groups comprising a single heating stage and providing heating to a fixed maximum temperature.

14. The portable intravenous fluid warming system of claim 13 wherein said group comprises at least two heating stages.

15. The portable intravenous fluid warming system of claim 9 wherein said microprocessor provides operational data from said system in ASCII format and further comprising means for displaying said data.

16. The portable intravenous fluid warming system of claim 15 and further comprising means for recording said data.

17. The portable intravenous fluid warming system of claim 9 wherein said heater system is a closed loop, progressive integrated, differential staged control system.

18. The portable intravenous fluid warming system of claim 9 and further comprising:

a data connector connected to said microprocessor; and an input means connected to said data connector for communicating with said microprocessor, said input means for adjusting the temperature of the fluid.

19. The portable intravenous fluid warming system of claim 9 wherein said system will maintain a preset temperature to within ±2° F. at an input/output flow rate of between approximately 1 milliliter per minute and approximately 200 milliliters per minute.

20. The portable intravenous fluid warming system of claim 1 further including a power jack in said housing for coupling to an external power source.

21. The portable intravenous fluid warming system of claim 1 further including an insulated covering disposed about said heating elements.

22. The portable intravenous fluid warming system of claim 1 wherein said tube sections are formed of stainless steel.

23. The portable intravenous fluid warming system of claim 1 wherein at least some of said interconnected tube sections are coated with heparin.

* * * * *